(12) United States Patent
Dickerson et al.

(10) Patent No.: US 11,051,839 B2
(45) Date of Patent: *Jul. 6, 2021

(54) ULTRASONIC SURGICAL INSTRUMENT WITH SLIDABLE FLEXING ACTIVATION MEMBER

(71) Applicant: Ethicon LLC, Guaynabo, PR (US)

(72) Inventors: Benjamin D. Dickerson, Cincinnati, OH (US); Cory G. Kimball, Hamilton, OH (US); Tylor C. Muhlenkamp, Cincinnati, OH (US); Kristen G. Denzinger, Cincinnati, OH (US); Chester O. Baxter, III, Cincinnati, OH (US); Ashvani K. Madan, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/276,704

(22) Filed: Feb. 15, 2019

(65) Prior Publication Data

US 2019/0247074 A1 Aug. 15, 2019

Related U.S. Application Data

(63) Continuation of application No. 14/836,383, filed on Aug. 26, 2015, now Pat. No. 10,258,361.

(51) Int. Cl.
*A61B 17/32* (2006.01)
*A61B 18/00* (2006.01)
(Continued)

(52) U.S. Cl.
CPC .......... *A61B 17/320068* (2013.01); *A61B 2017/00367* (2013.01); *A61B 2017/00389* (2013.01);
(Continued)

(58) Field of Classification Search
CPC .... A61B 17/320068; A61B 2017/2918; A61B 2017/00367; A61B 2017/00424; A61B 2017/00017; A61B 2018/00916
See application file for complete search history.

(56) References Cited

U.S. PATENT DOCUMENTS 4,088,855 A * 5/1978 Emery ............... H01H 1/242
200/16 A
5,322,055 A 6/1994 Davison et al.
(Continued)

FOREIGN PATENT DOCUMENTS

CN 103315779 A 9/2013
CN 104248463 A 12/2014
(Continued)

OTHER PUBLICATIONS

International Search Report and Written Opinion dated Sep. 28, 2016 for International Application No. PCT/US2016/047168, 13 pages.

(Continued)

*Primary Examiner* — Majid Jamialahmadi
(74) *Attorney, Agent, or Firm* — Frost Brown Todd LLC

(57) ABSTRACT

An ultrasonic instrument for use during a surgical procedure includes a body, a shaft assembly, an ultrasonic blade, and an actuation assembly. The body is configured to receive an ultrasonic transducer for selectively generating a first or a second predetermined oscillation. The shaft assembly projects from the body and includes an acoustic waveguide connected to the ultrasonic blade. The actuation assembly includes an activator ring and an activation mechanism. The activator ring is selectively movable along the body such that the activator ring is accessible to be gripped by an operator around an entirety of an outer circumferential surface of the activator ring. The activation mechanism is connected to the activator ring such that the activation (Continued)

mechanism selectively moves along the body in conjunction with the activator ring. At least a portion of the activation mechanism is configured to selectively direct the ultrasonic transducer to oscillate the ultrasonic blade.

20 Claims, 8 Drawing Sheets

(51) Int. Cl.
 *A61B 17/00* (2006.01)
 *A61B 17/29* (2006.01)
(52) U.S. Cl.
 CPC .......... *A61B 2017/2918* (2013.01); *A61B 2018/00178* (2013.01)

(56) References Cited

U.S. PATENT DOCUMENTS

| | | | |
|---|---|---|---|
| 5,324,299 | A | 6/1994 | Davison et al. |
| 5,873,873 | A | 2/1999 | Smith et al. |
| 5,980,510 | A | 11/1999 | Tsonton et al. |
| 6,283,981 | B1 | 9/2001 | Beaupre |
| 6,309,400 | B2 | 10/2001 | Beaupre |
| 6,325,811 | B1 | 12/2001 | Messerly |
| 6,423,082 | B1 | 7/2002 | Houser et al. |
| 6,773,444 | B2 | 8/2004 | Messerly |
| 6,783,524 | B2 | 8/2004 | Anderson et al. |
| 6,945,981 | B2 | 9/2005 | Donofrio et al. |
| 8,057,498 | B2 | 11/2011 | Robertson |
| 8,152,825 | B2 | 4/2012 | Madan et al. |
| 8,461,744 | B2 | 6/2013 | Wiener et al. |
| 8,591,536 | B2 | 11/2013 | Robertson |
| 8,623,027 | B2 | 1/2014 | Price et al. |
| 8,911,460 | B2 | 12/2014 | Neurohr et al. |
| 8,986,302 | B2 | 3/2015 | Aldridge et al. |
| 9,023,071 | B2 | 5/2015 | Miller et al. |
| 9,095,367 | B2 | 8/2015 | Olson et al. |
| 9,381,058 | B2 | 7/2016 | Houser et al. |
| 9,393,037 | B2 | 7/2016 | Olson et al. |
| 10,258,361 | B2* | 4/2019 | Dickerson ...... A61B 17/320068 |
| 2002/0049464 | A1 | 4/2002 | Donofrio et al. |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2010/0069940 | A1* | 3/2010 | Miller ............ A61B 17/320068 606/169 |
| 2012/0116265 | A1 | 5/2012 | Houser et al. |
| 2012/0116395 | A1* | 5/2012 | Madan ............... A61B 18/1445 606/45 |
| 2015/0080924 | A1 | 3/2015 | Stulen et al. |
| 2015/0148829 | A1* | 5/2015 | Kimball ................ A61B 90/03 606/169 |
| 2015/0148830 | A1 | 5/2015 | Stulen et al. |
| 2016/0022305 | A1 | 1/2016 | Lamping et al. |
| 2016/0074060 | A1 | 3/2016 | Messerly et al. |

FOREIGN PATENT DOCUMENTS

| | | | |
|---|---|---|---|
| CN | 104582617 | A | 4/2015 |
| DE | 2460481 | A1 | 6/1976 |
| EP | 2574293 | A3 | 4/2013 |
| WO | WO 1996/024298 | A1 | 8/1996 |
| WO | WO 2014/047245 | A1 | 3/2014 |
| WO | WO 2015/046349 | A1 | 4/2015 |

OTHER PUBLICATIONS

U.S. Appl. No. 61/410,603, filed Nov. 5, 2010.
Chinese Office Action, The First Office Action, and First Search dated Jun. 2, 2020 for Application No. CN 201680062579.1, 16 pgs.
Brazilian Search Report dated Jun. 16, 2020 for Application No. BR 112018003696-0, 4 pgs.
Japanese Office Action, Notice of Reasons for Refusal, and Search Report dated Sep. 8, 2020 for Application No. JP 2018-510496, 30 pgs.

* cited by examiner

ULTRASONIC SURGICAL INSTRUMENT WITH SLIDABLE FLEXING ACTIVATION MEMBER

This application is a continuation of U.S. patent application Ser. No. 14/836,383, filed Aug. 26, 2015 and issued as U.S. Pat. No. 10,258,361 on Apr. 16, 2019.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2104, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat. No. 9,095,367 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
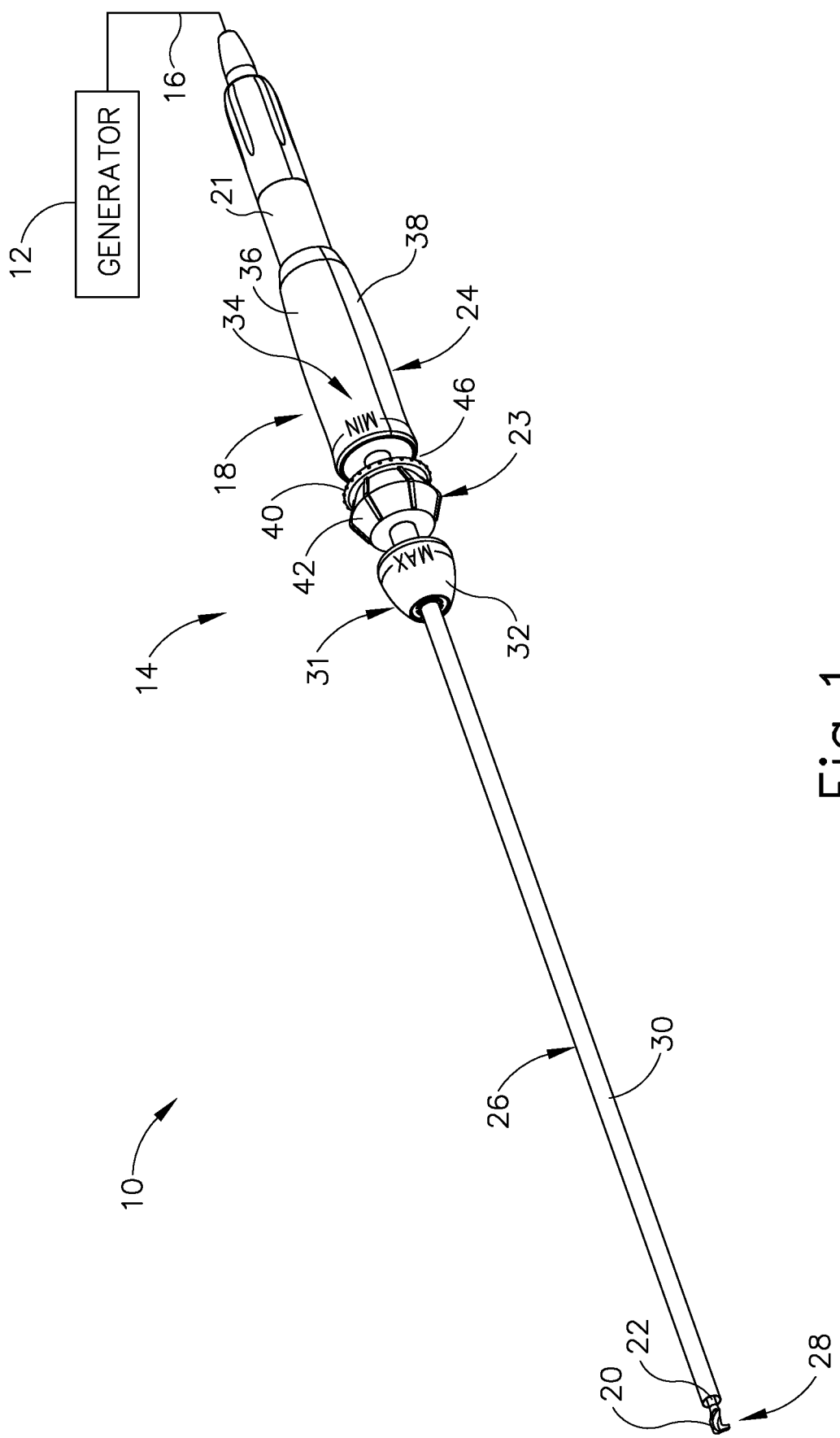
FIG. 1 depicts a perspective view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. OVERVIEW OF EXEMPLARY ULTRASONIC SURGICAL SYSTEM

FIG. 1 shows components of an exemplary surgical system (10). As shown, the surgical system (10) comprises an ultrasonic generator (12) and an ultrasonic surgical instrument (14). As will be described in greater detail below, the surgical instrument (14) is operable to cut tissue and seal or weld tissue (e.g., a blood vessel, etc.) substantially simultaneously, using ultrasonic vibrational energy. The generator (12) and the surgical instrument (14) are coupled together via a cable (16). The cable (16) may comprise a plurality of wires; and may provide unidirectional electrical communication from the generator (12) to the surgical instrument (14) and/or bidirectional electrical communication between the generator (12) and the surgical instrument (14). By way of example only, the cable (16) may comprise a "hot" wire for electrical power to the surgical instrument (14), a ground wire, and a signal wire for transmitting signals from the surgical instrument (14) to the ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of the surgical system (10) may incorporate the generator (12) into the surgical instrument (14), such that the cable (16) may simply be omitted.

By way of example only, the ultrasonic generator (12) may comprise the GEN04, GEN11, or GEN 300 sold by Ethicon Endo-Surgery, Inc. of Cincinnati, Ohio. In addition or in the alternative, the ultrasonic generator (12) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Alternatively, any other suitable generators may be used. As will be described in greater detail below, the ultrasonic generator (12) is operable to provide power to the surgical instrument (14) to perform ultrasonic surgical procedures.

The surgical instrument (14) comprises a handpiece (18), which is configured to be grasped in one hand (or two hands) of an operator and manipulated by one hand (or two hands) of the operator during a surgical procedure. For instance, in some versions, the handpiece (18) may be grasped like a pencil by the operator. In some other versions, the handpiece (18) may include a scissor grip that may be grasped like scissors by the operator. In some other versions, the handpiece (18) may include a pistol grip that may be grasped like a pistol by the operator. Of course, the handpiece (18) may be configured to be gripped in any other suitable fashion. Furthermore, some versions of the surgical instrument (14) may substitute the handpiece (18) with an alternative body (not shown) coupled to a robotic surgical system (not shown) configured to operate an alternative instrument, such as by remote control. In the present example, a blade (20) extends distally from the handpiece (18). The handpiece (18) includes an ultrasonic transducer (21) and an ultrasonic waveguide (22), which couples the ultrasonic transducer (21) with the blade (20). The ultrasonic transducer (21) receives electrical power from the generator (12) via the cable (14) and, by virtue of its piezoelectric properties, the ultrasonic transducer (21) converts such electrical power into ultrasonic vibrational energy. When the ultrasonic transducer (21) of the present example is activated, these mechanical oscillations are transmitted through the waveguide (22) to reach the blade (20), thereby providing oscillation of the blade (20) at the resonant ultrasonic frequency.

Thus, the ultrasonic oscillation of the blade (20) may simultaneously sever the tissue and denature the proteins in adjacent tissue cells, thereby providing a coagulative effect with relatively little thermal spread. In some versions, an electrical current may also be provided through the blade (20) to also cauterize the tissue.

By way of example only, the ultrasonic waveguide (22) and the blade (20) may comprise components sold under product codes SNGHK and SNGCB by Ethicon Endo-Surgery, Inc. of Cincinnati, Ohio. By way of further example only, the ultrasonic waveguide (22) and/or the blade (20) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, the ultrasonic waveguide (22) and/or the blade (20) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of the ultrasonic waveguide (22) and the blade (20) will be apparent to those of ordinary skill in the art in view of the teachings herein.

The handpiece (18) of the present example also includes an actuation assembly (23) in communication with a circuit board (not shown). By way of example only, the circuit board (not shown) may comprise a conventional printed circuit board, a flex circuit, a rigid-flex circuit, or may have any other suitable configuration. The actuation assembly (23) may be in communication with the circuit board (not shown) via one or more wires, traces formed in a circuit board or flex circuit, and/or in any other suitable fashion. The actuation assembly (23) is operable to selectively direct power from the generator (12) to the ultrasonic transducer (21) for operating the blade (20).

In the present example, the surgical system (10) is operable to provide at least two different levels or types of ultrasonic energy (e.g., different frequencies and/or amplitudes, etc.) at the blade (20). To that end, the actuation assembly (23) is operable to permit the operator to select a desired, predetermined oscillation of ultrasonic energy.

It should be understood that the predetermined oscillations provided at the blade (20) may be a function of characteristics of the electrical power communicated from the generator (12) to the surgical instrument (14) via the cable (16). Thus, the control circuitry (not shown) of the generator (12) may provide electrical power (via cable (16)) having characteristics associated with the ultrasonic energy level/amplitude or type selected through the actuation assembly (23). The generator (12) may thus be operable to communicate different types or degrees of electrical power to the ultrasonic transducer (21), in accordance with selections made by the operator via the actuation assembly (23). In particular, and by way of example only, the generator (12) may increase the voltage and/or current of the applied signal to increase the longitudinal amplitude of the acoustic assembly. As a merely illustrative example, the generator (12) may provide selectability between a maximum level and a minimum level, which may correspond with a blade vibrational resonance amplitude of approximately 50 microns and approximately 90 microns, respectively. Of course, it will be appreciated that other levels between and/or beyond maximum and minimum may be incorporated into the surgical instrument (18), as well.

In other examples, control circuitry (not shown) is located within the handpiece (18). For instance, the generator (12) may only communicate one type of electrical power (e.g., just one voltage and/or current available) to the handpiece (18) such that the control circuitry (not shown) within the handpiece (18) is operable to modify the electrical power (e.g., the voltage of the electrical power), in accordance with selections made by the operator, before the electrical power reaches the ultrasonic transducer (21). Furthermore, the generator (12) may be incorporated into the handpiece (18) along with all other components of the surgical system (10). For instance, one or more batteries (not shown) or other portable sources of power may be provided in the handpiece (18). Still other suitable ways in which the components depicted in FIG. 1 may be rearranged or otherwise configured or modified will be apparent to those of ordinary skill in the art in view of the teachings herein.

II. OVERVIEW OF EXEMPLARY ULTRASONIC SURGICAL INSTRUMENT

The following discussion relates to various exemplary components and configurations for the surgical instrument (14). It should be understood that the various examples of the surgical instrument (14) described below may be readily incorporated into the surgical system (10), as described above, or alternative surgical systems. It should also be understood that the various components and operability of the surgical instrument (14) described above may be readily incorporated into the exemplary versions of the surgical instrument (14) described below. Various suitable ways in which the above and below teachings may be combined will be apparent to those of ordinary skill in the art in view of the teachings herein. It should also be understood that the below teachings may be readily combined with the various teachings of the references that are cited herein.

Figure 2:
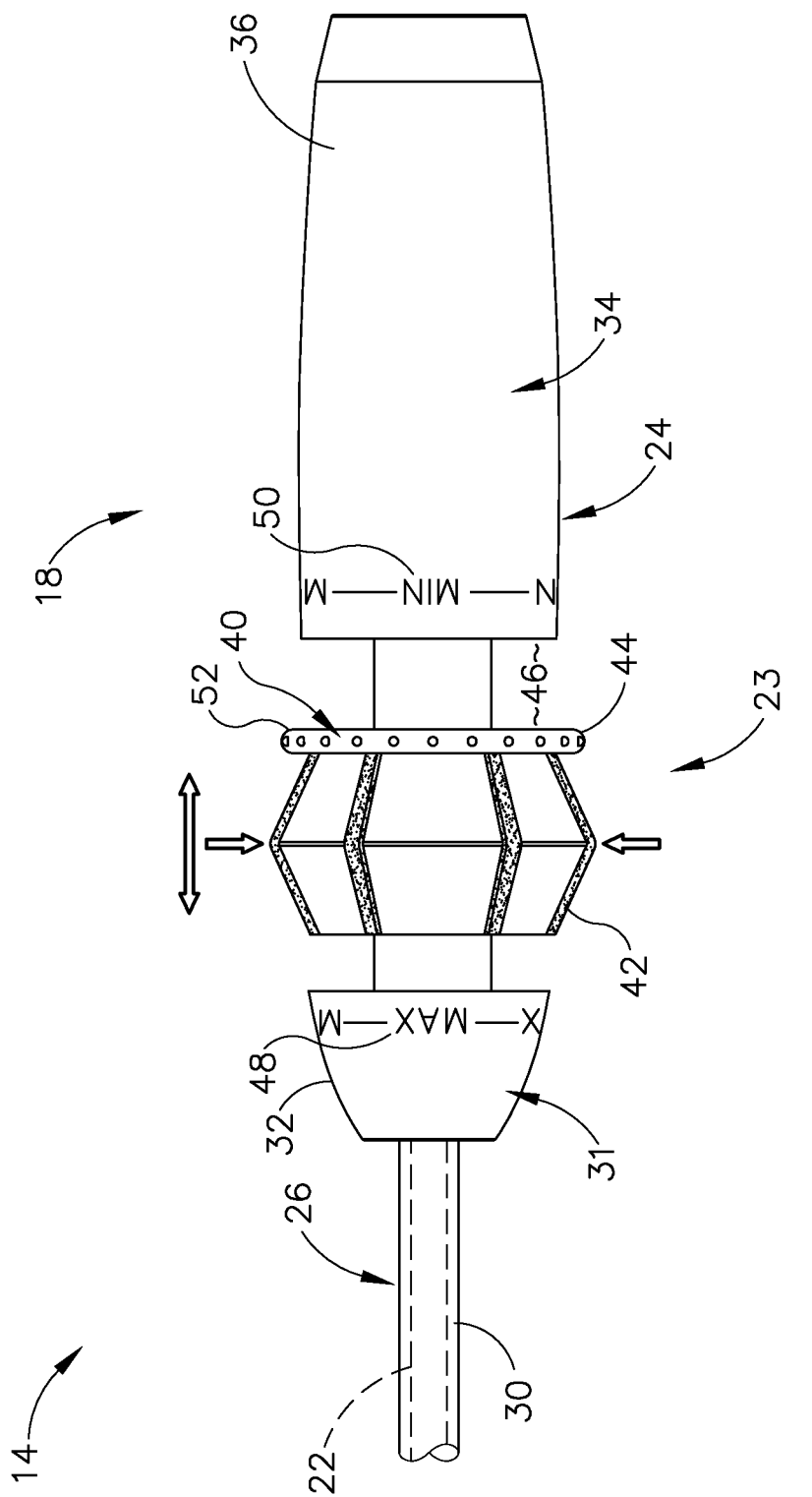
FIG. 2 depicts a top view of a handle assembly of the surgical instrument of FIG. 1, with an actuation assembly in a neutral position.

FIGS. 1-3 illustrate the exemplary ultrasonic surgical instrument (14). At least part of the surgical instrument (14) may be constructed and operable in accordance with at least some of the teachings of U.S. Pat. Nos. 5,322,055; 5,873,873; 5,980,510; 6,325,811; 6,773,444; 6,783,524; 8,461,744; U.S. Pub. No. 2009/0105750, issued as U.S. Pat. No. 8,623,027 on Jan. 7, 2014; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pat. Pub. No. 2014/0114334, issued as U.S. Pat. No. 9,095,367 on Aug. 4, 2015; U.S. patent application Ser. No. 14/028,717, issued as U.S. Pat. No. 10,172,636 on Jan. 8, 2019; and/or U.S. Pat. App. No. 61/410,603. The disclosures of each of the foregoing patents, publications, and applications are incorporated by reference herein. As described therein and as will be described in greater detail below, the surgical instrument (14) is operable to cut tissue and seal or weld tissue substantially simultaneously. It should also be understood that the surgical instrument (14) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, the surgical instrument (14) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to the surgical instrument (14), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

The surgical instrument (14) is configured to be used as a scalpel. As shown in FIGS. 1-2, the surgical instrument (14) of this example comprises a handle assembly (24), a shaft assembly (26), an end effector (28), and the actuating assembly (23). In the present example, a proximal end of the surgical instrument (14) operatively connects to the ultrasonic transducer (21) by insertion of the ultrasonic transducer (21) into the handle assembly (24). The handle assembly (24) receives the ultrasonic transducer (21) such that the ultrasonic transducer (21) couples to the waveguide (22) in the shaft assembly (26) by a threaded connection, though any other suitable connection for such coupling may be used. As shown in FIGS. 1-2, the surgical instrument (14) may be coupled with the ultrasonic transducer (12) to form a single unit.

A. Exemplary Shaft Assembly and End Effector

As best seen in FIGS. 1-2, the shaft assembly (26) comprises an outer sheath (30) with the waveguide (22) disposed within the outer sheath (30). In some versions, the outer sheath (30) and the waveguide (22) are sized to fit through a trocar or other minimally invasive access port, such that the surgical instrument (14) may be used in a minimally invasive surgical procedure. The waveguide (22) is configured to transmit ultrasonic vibrations from the ultrasonic transducer (21) to the blade (20). By way of example only, the shaft assembly (26), the end effector (28), and the waveguide (22) may be constructed in accordance with at least some of the teachings of U.S. patent application Ser. No. 14/337,508, entitled "Ultrasonic Blade Overmold," filed Jul. 22, 2014, issued as U.S. Pat. No. 9,750,521 on Sep. 5, 2017, the disclosure of which is incorporated by reference herein.

The surgical instrument (14) lacks a clamp arm in this example, such that surgical instrument (14) is configured for use as an ultrasonic scalpel for simultaneously slicing and cauterizing tissue. Instead, the end effector (28) merely consists of the blade (20) that may be used for simultaneously slicing and cauterizing tissue. In some alternative versions, including but not limited to those described below, the end effector (28) may include a clamp arm (not shown) that may be used to compress tissue against the blade (20) to assist in grasping, sealing, and/or cutting the tissue. Such a clamp arm (not shown) may be removably coupled to surgical instrument (14). By way of example only, the removable clamp arm (not shown) may be provided in accordance with at least some of the teachings of U.S. patent application Ser. No. 14/488,330, entitled "Ultrasonic Surgical Instrument with Removable Clamp Arm," filed Sep. 17, 2014, issued as U.S. Pat. No. 10,058,346 on Aug. 28, 2018, the disclosure of which is incorporated by reference herein. Alternatively, a clamp arm may be provided in any other suitable fashion.

B. Exemplary Handle Assembly

As best seen in FIGS. 1-2, the handle assembly (24) comprises a torquing mechanism (31), which includes a rotation knob (32), and a tubular elongate body (34). The torquing mechanism (31) is configured to limit the amount of torque that can be applied between the shaft assembly (26) and the ultrasonic transducer (21) and will be discussed below in additional detail. The elongate body (34) is configured to permit a user to grip the handle assembly (24) from a variety of positions, while the user operates the actuation assembly (23) of the handpiece (18) from these respective positions. The exemplary actuation assembly (23) will be discussed below in additional detail.

By way of example only, the handle assembly (24) may be shaped to be grasped and manipulated in a pencil-grip arrangement, in a screwdriver-grip arrangement, and/or in any other suitable fashion. The elongate body (34) of the present example comprises a pair of mating housing portions (36, 38), though it should be understood that the handle assembly (24) may alternatively comprise just a single housing component. The housing portions (36, 38) may be constructed from a durable plastic, such as polycarbonate or a liquid crystal polymer. It is also contemplated that the housing portions (36, 38) may alternatively be made from a variety of materials or combinations of materials, including but not limited to other plastics, ceramics, and/or metals, etc.

In the present example, the elongate body (34) of the handle assembly (24) includes a proximal end, a distal end, and a cavity (not shown) extending longitudinally therein. The cavity (not shown) is configured to accept at least a portion of the actuation assembly (23) and at least a portion of the ultrasonic transducer (21). To this end, one or more electrical contacts (not shown) of the ultrasonic transducer (21) operatively connect with the actuation assembly (23) to provide the operator with finger-activated controls on the surgical instrument (14). More particularly, the ultrasonic transducer (21) of the present example includes two conductive rings (not shown) that are securely disposed within the elongate body (34) of the ultrasonic transducer (21). By way of example only, such conductive rings and/or other features of the ultrasonic transducer (21) may be provided in accordance with at least some of the teachings of U.S. Pat. No. 8,152,825, entitled "Medical Ultrasound System and Handpiece and Methods for Making and Tuning," issued Apr. 10, 2012, the disclosure of which is incorporated by reference herein.

With respect to FIGS. 1-2, the cavity (not shown) also contains a switch assembly (not shown). The switch assembly (not shown) provides an electro-mechanical interface between the actuation assembly (23) and the generator (12) via the ultrasonic transducer (21) and an ultrasonic transducer circuit (42). By way of example, the switch assembly (not shown) may comprise a plurality of contact switches (not shown), such as electrical contact switches, for selectively directing operation the surgical system (10), Such electrical contact switches provide an electrical signal to the generator (12) and/or closes a circuit between the generator (12) and the ultrasonic transducer (21). By way of example only, various components of the switch assembly (not shown) may operatively connect to the ultrasonic transducer (21), such as by ring conductors (not shown) of the ultrasonic transducer (21). Thus, when one or more of the contact switches (not shown) are actuated, the generator (12) activates the ultrasonic transducer (21) to generate ultrasonic vibrations.

As mentioned above, the ultrasonic transducer (21) threadably couples with the waveguide (22) of the shaft assembly (26) in this example. The proximal end of the shaft assembly (26) comprises the torquing mechanism (31) configured to permit coupling of the waveguide (22) with the ultrasonic transducer (21); while at the same time limiting the amount of torque that can be applied to the shaft assembly (26) and/or the ultrasonic transducer (21). By way of example, the torquing mechanism (31) comprises the rotation knob (32), an annular rack (not shown), and a wave spring (not shown). More particularly, the rotation knob (32) is rotatably disposed about the shaft assembly (26) such that the rotation knob (32) may be rotated about the shaft assembly (26).

During an initial stage of assembly of the surgical instrument (14), an operator may first align the ultrasonic transducer (21) along a longitudinal axis shared by the handle assembly (24) and the shaft assembly (26), then insert the ultrasonic transducer (21) into the proximal end of the handle assembly (24). The wave spring (not shown) will ensure initial contact between the distal end of the ultrasonic transducer (21) and the proximal end of the waveguide (22) as the ultrasonic transducer (21) is inserted into the handle assembly (24). The operator may then grasp the ultrasonic transducer (21) with one hand and grasp either the handle assembly (24) or the rotation knob (32) with the other hand. Once these components are firmly grasped, the operator may rotate the handle assembly (24) or the rotation knob (32) relative to the ultrasonic transducer (21) about the longitudinal axis. As such, the handle assembly (24), the rotation knob (32), and the shaft assembly (26) will all rotate together concurrently relative to the ultrasonic transducer (21).

As the handle assembly (24) and the shaft assembly (26) rotate relative to the ultrasonic transducer (21), the waveguide (22) is threaded onto the ultrasonic transducer (21) until the waveguide (22) encounters a predetermined resistance to further rotation. The predetermined resistance indicates that the ultrasonic transducer (21) and the waveguide (22) are operatively connected at a predetermined torque level. As such, the torquing assembly (31) is configured to act as a slip clutch and restrict the amount of torque by which the waveguide (22) may be coupled with the ultrasonic transducer (21).

It should be understood that the above described example of torquing mechanism (31) is merely illustrative. The torquing mechanism (31) may be constructed and operable in any other suitable fashion. By way of example only, the torquing mechanism (31) may be constructed and operable in accordance with at least some of the teachings of U.S. patent application Ser. No. 14/087,383, entitled "Features for Coupling Surgical Instrument Shaft Assembly with Instrument Body," filed on Nov. 22, 2013, issued as U.S. Pat. No. 10,368,892 on Aug. 6, 2019, the disclosure of which is incorporated by reference herein. Other suitable ways in which the torquing mechanism (31) may be constructed and operable will be apparent to those of ordinary skill in the art in view of the teachings herein.

The surgical instrument (14) may further be configured and operable in accordance with the teachings of U.S. Pub. No. 2008/0200940, entitled "Ultrasonic Energy Device for Cutting and Coagulating," published Aug. 21, 2008, now abandoned, the disclosure of which is incorporated by reference herein. Alternatively, the surgical instrument (14) may be provided with a variety of other components, configurations, and/or types of operability as will be apparent to those of ordinary skill in the art in view of the teachings herein.

In addition to or in lieu of being constructed in accordance with the above teachings, at least part of the surgical instrument (14) may be constructed and operable in accordance with at least some of the teachings of U.S. Pat. Nos. 5,322,055; 5,873,873; 5,980,510; 6,283,981; 6,309,400; 6,325,811; 6,423,082; 6,783,524; 8,057,498; 8,461,744; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2008/0234710, issued as U.S. Pat. No. 8,911,460 on Dec. 16, 2014; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; and/or U.S. Pat. App. No. 61/410,603. The disclosures of each of the foregoing patents, publications, and applications are incorporated by reference herein. Additional merely illustrative variations for the surgical instrument (14) will be apparent to those of ordinary skill in the art in view of the teachings herein. It should be understood that the below described variations may be readily applied to the surgical instrument (14) described above and any of the instruments referred to in any of the references that are cited herein, among others.

C. Exemplary Actuation Assembly

FIGS. 1-2 show one example of the actuation assembly (23) that connects with the switch assembly (not shown) for both selecting between at least two predetermined ultrasonic power levels and activating the surgical instrument (14) accordingly. The actuation assembly (23) includes an activator element in the form of an activator ring (40); and an activation mechanism in the form of a collapsible activation collar (42). To this end, the activator ring (40) is configured to selectively move along the elongate body (34) and be accessible to the operator from around an entirety of an outer circumferential surface (44) of the activator ring (40). The activation collar (42) connects to the activator ring (40) such that the activation collar (42) simultaneously moves with the activator ring (40) for similar operator access. At least a portion of the activation collar (42) is configured to selectively activate the ultrasonic transducer (21) to thereby drive the ultrasonic blade (20) to vibrate at the selected ultrasonic power level.

The activator ring (44) and the activation collar (42) generally surround the elongate body (34) and are received within an annular groove (46) encircling the elongate body (34). The activator ring (44) and the activation collar (42) similarly encircle the longitudinal axis and are coaxially aligned with the longitudinal axis. In the present example, the activator ring (44) and the activation collar (42) both extend 360 degrees about the longitudinal axis. In some other versions, the activator ring (44) and/or the activation collar (42) extend about the longitudinal axis for less than 360 degrees. For instance, the activator ring (44) and/or the activation collar (42) may extend along an arc spanning approximately 90 degrees, 180 degrees, or 270 degrees about the longitudinal axis. In such versions, the arc along which the activator ring (44) and/or the activation collar (42) extends may have a constant radius along that angular range.

In order to select between the at least two predetermined ultrasonic power levels, the activator ring (44) and the activation collar (42) are translatably mounted against the elongate body (34) and are configured to collectively translate along the longitudinal axis within the annular groove (46). More particularly, the activator ring (44) and the activation collar (42) collectively translate between a distal position, an intermediate position, and a proximal position. By way of example, the activator ring (44) and the activation collar (42) in the distal position is a maximum power position, whereas the proximal position is a minimum power position. In the intermediate position as shown in FIGS. 1-2, activator ring (44) and activation collar (42) are configured to prevent activation of the ultrasonic transducer (21) and blade (20). The intermediate position may also be referred to as an off position. The maximum and minimum power positions as well as the off position described herein indicate unique modes of operating the surgical instrument (14) during the surgical procedure.

While the terms "maximum" and "minimum" are used herein, it should be understood that these do not necessarily indicate the maximum and minimum ultrasonic power levels that the ultrasonic transducer (21) is theoretically capable of operating at. These only indicate the maximum and minimum ultrasonic power levels that are made available to the operator of instrument (14). It should also be understood that instrument (14) may provide various other ultrasonic power levels for the operator to choose from, such that the availability does not need to be limited to a "maximum" power level and a "minimum" power level.

The elongate body (34) further includes a plurality of indicia (48, 50) configured to indicate to the operator the selected mode of operation unique to the maximum and minimum positions. The rotation knob (32) has a "MAX" indicia (48) adjacent to the distal end of the annular groove (46), whereas the elongate body (34) has a "MIN" indicia (50) adjacent to the proximal end of the annular groove (46). As such, translating the activator ring (44) and the activation collar (42) toward the "MAX" indicia (48) to the distal end of the annular groove (46) indicates to the operator that the actuation assembly (23) is in the minimum position, such that the ultrasonic transducer (21) will provide the maximum ultrasonic power level to the ultrasonic blade (20). Similarly, translating the activator ring (44) and the activation collar (42) toward the "MIN" indicia (50) to the proximal end of the annular groove (46) indicates to the operator that the actuation assembly (23) is in the minimum position, such that the ultrasonic transducer (21) will provide the minimum ultrasonic power level to the ultrasonic blade (20). While these plurality of indicia (48, 50) show one example for indicating operation of the surgical instrument (18), it will be appreciated that alternative indicia may be used to similarly communicate the intended operation to the operator. As such, these examples are not intended to unnecessarily limit the invention described herein.

With respect to FIG. 2, the activation collar (42) extends distally from the activator ring (40), which includes an annular lip (52). Thereby, the operator may grip the activation collar (42) with one or more fingers, while simultaneously gripping the annular lip (52) with one or more of the remaining fingers. Alternatively, in another example, the activation collar (42) may extend proximally from the activator ring (40) for an alternative grip. It will be appreciated that other alternatives for connecting the activation collar (42) to the activator ring (40) may be further used for providing a location by which the operator my grip the actuation assembly (23).

The selective translation of the activator ring (40) with the activation collar (42) is generally configured to actuate a selector switch (not shown), which operatively directs the selection between the plurality of predetermined ultrasonic power levels. In contrast, pressing inwardly on the activation collar (42) actuates an activation switch (not shown), which directs the generator (12) (see FIG. 1) to power the ultrasonic transducer (21) (see FIG. 1) and generate the ultrasonic oscillations at the power level selected via the selector switch (not shown). To this end, the exemplary activation collar (42) shown in FIG. 2 is compressible from an expanded state to a contacted state for actuating the activation switch (not shown). According to one example, the activation collar (42) is biased radially outwardly from the longitudinal axis in the expanded state. The operator radially compresses the activation collar (42) inwardly toward the longitudinal axis (e.g., by pinching the activation collar (42) or otherwise pressing inwardly on collar (42)) in order to actuate the activation switch (not shown) in the contracted state and thereby activate the blade (20) (see FIG. 1). In turn, releasing the activation collar (42) allows the activation collar (42) to return outwardly to the expanded state and thereby deactivate the blade (20) (see FIG. 1). Thus, the activation collar (42) is configured to inhibit the ultrasonic transducer (21) (see FIG. 1) from oscillating the blade (20) (see FIG. 1) in the expanded state unless activation collar (42) is being selectively compressed by the operator.

In some versions, an inner surface (not shown) of the activation collar (42) includes a set of electrically conductive features (not shown), while the elongate body (34) within the annular groove (46) includes another set of complementary electrically conductive features (not shown). Compressing the activation collar (42) toward the elongate body (34) thereby brings these sets of complementary electrically conductive features (not shown) in contact with each other in order to close an activation circuit of the control circuitry (not shown) of the surgical instrument (14) and thereby activate the ultrasonic generator (21) (see FIG. 1), thereby activating the ultrasonic transducer (21). Alternatively, the handpiece (18) may include a distal set of thin film switches (not shown) within in the groove (46) and a proximal set of thin film switches (not shown) within the groove (46). The distal and proximal switches (not shown) may thus be actuated when the activation collar (42) is compressed to the contracted state for closing the activation circuit in control circuitry (not shown). Other suitable features and configurations that may be used to provide activation of the ultrasonic transducer (21) (see FIG. 1) in response to compression of activation collar (42) will be apparent to those of ordinary skill in the art in view of the teachings herein.

As shown in FIG. 2, the activator ring (44) and activation collar (42) in the off position are configured to prevent activation of the ultrasonic generator (21) (see FIG. 1) (and, hence, the ultrasonic transducer (21)) despite compression of the activation collar (42). For example, the activation circuit of the control circuitry (not shown) may be configured to be in an open state when activator ring (44) and activation collar (42) in the off position. For instance, complementary electrical contacts may be non-aligned with each other such that they will not come into contact with each other when activation collar (42) is compressed while in the off position. As another merely illustrative example, activation collar (42) may be configured such that it does not actuate thin film switches within the groove (46) when activation collar (42) is compressed while in the off position. Thus, the activation circuit of the control circuitry (not shown) of the present example will always remain in an open state when the activator ring (44) and activation collar (42) are in the off position, thereby preventing activation of the ultrasonic generator (21) (and, hence, the ultrasonic transducer (21)).

With respect to FIGS. 3A-4B, the operator grips the actuation assembly (23) with at least one hand for translating the actuation assembly (23) within the annular grove (46). The operator has access to the actuation assembly (23) from around generally the entirety of the surgical instrument (14) given that the actuation assembly (23) generally surrounds the elongate body (34). Thereby, the operator may activate the surgical instrument (14) as described below from a variety of angles during the surgical procedure for improved ease of use.

Figure 3A:
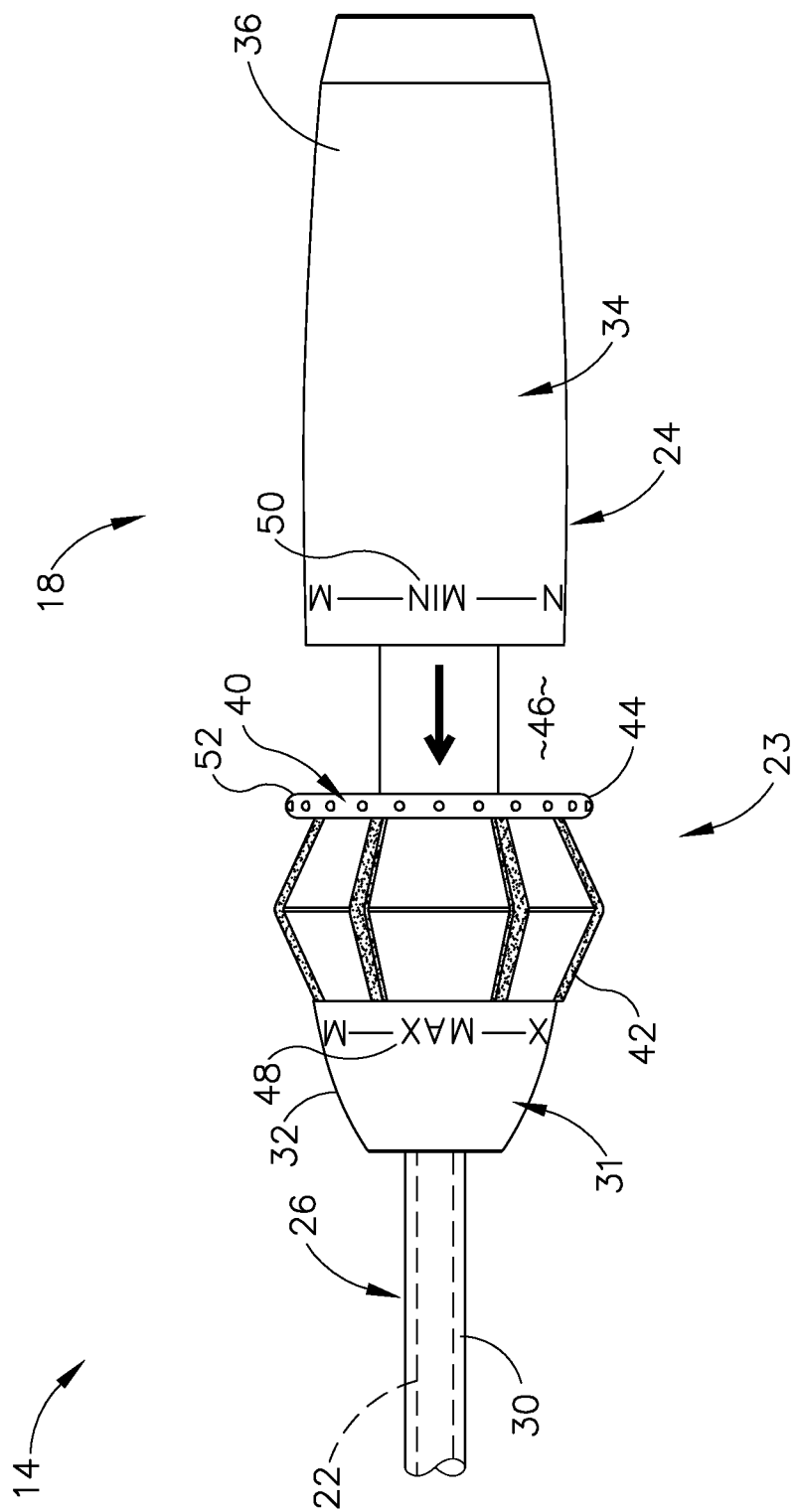
FIG. 3A depicts a top view of an inactivated handle assembly of the surgical instrument of FIG. 1, with the actuation assembly in a maximum power position and in a non-actuated state.
Figure 3B:
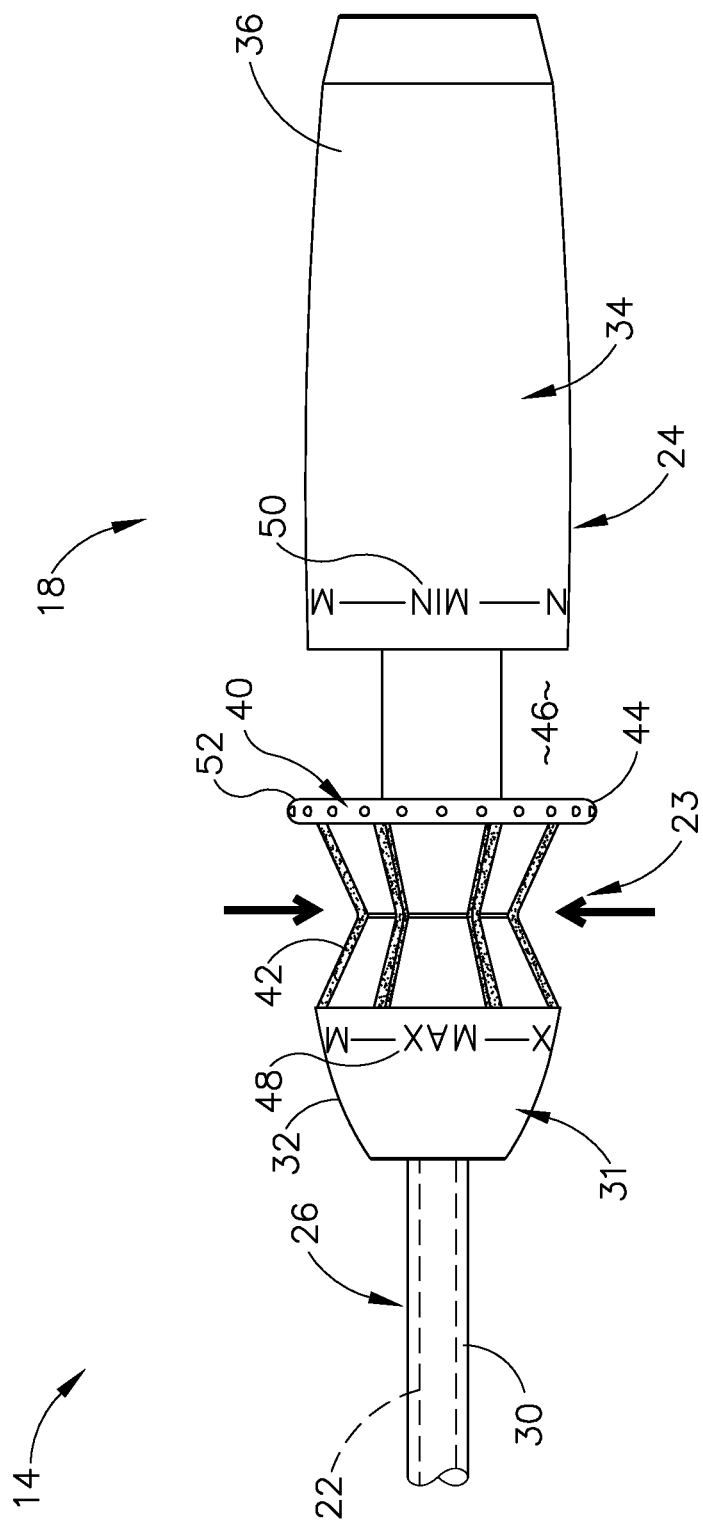
FIG. 3B depicts a top view of an activated handle assembly of the surgical instrument of FIG. 1, with the actuation assembly in the maximum power position and in an actuated state.

FIGS. 3A-3B show one example of the surgical instrument (14) in use to provide the high ultrasonic power level during the surgical procedure. With respect to FIG. 3A, the operator selects the high power position. If the actuation assembly (23) is not already in the high power position, the operator translates the actuation assembly (23) distally to the distal end of the annular groove (46) in order to select the high power position. To activate the blade (20) (see FIG. 1), the operator compresses the activation collar (42) from the expanded state, shown in FIG. 3A, to the contracted state in FIG. 3B in order to close the activation circuit in control circuitry (not shown), as discussed above. The operator may then release the activation collar (42) to deactivate the blade (20). Alternatively, rather than release the activation collar (42), the operator may translate the actuation assembly (23) proximally to the low power position to activate the blade (20) at the low ultrasonic power level.

Figure 4A:
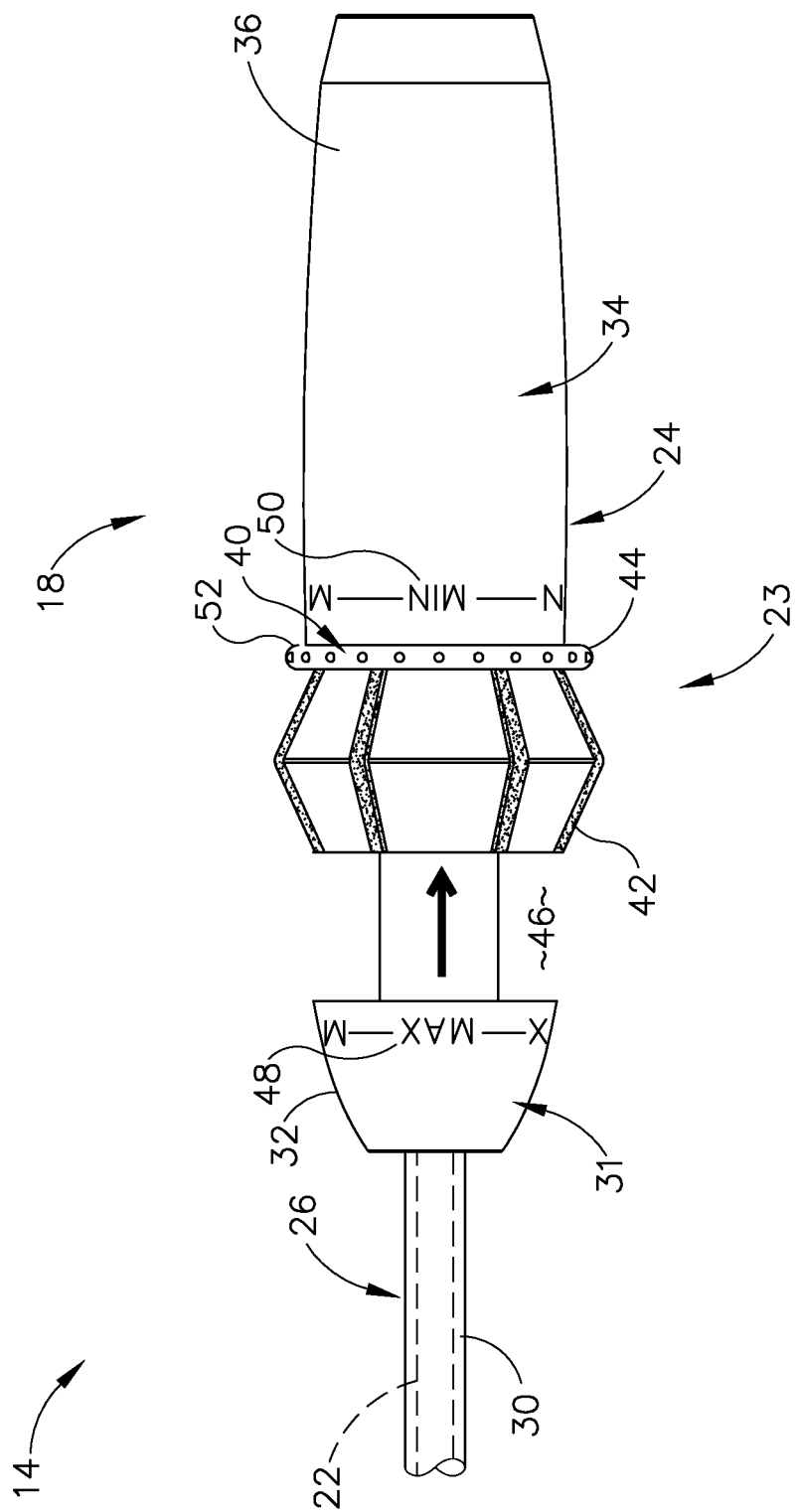
FIG. 4A depicts a top view of an inactivated handle assembly of the surgical instrument of FIG. 1, with the actuation assembly in a minimum power position and in a non-actuated state.
Figure 4B:
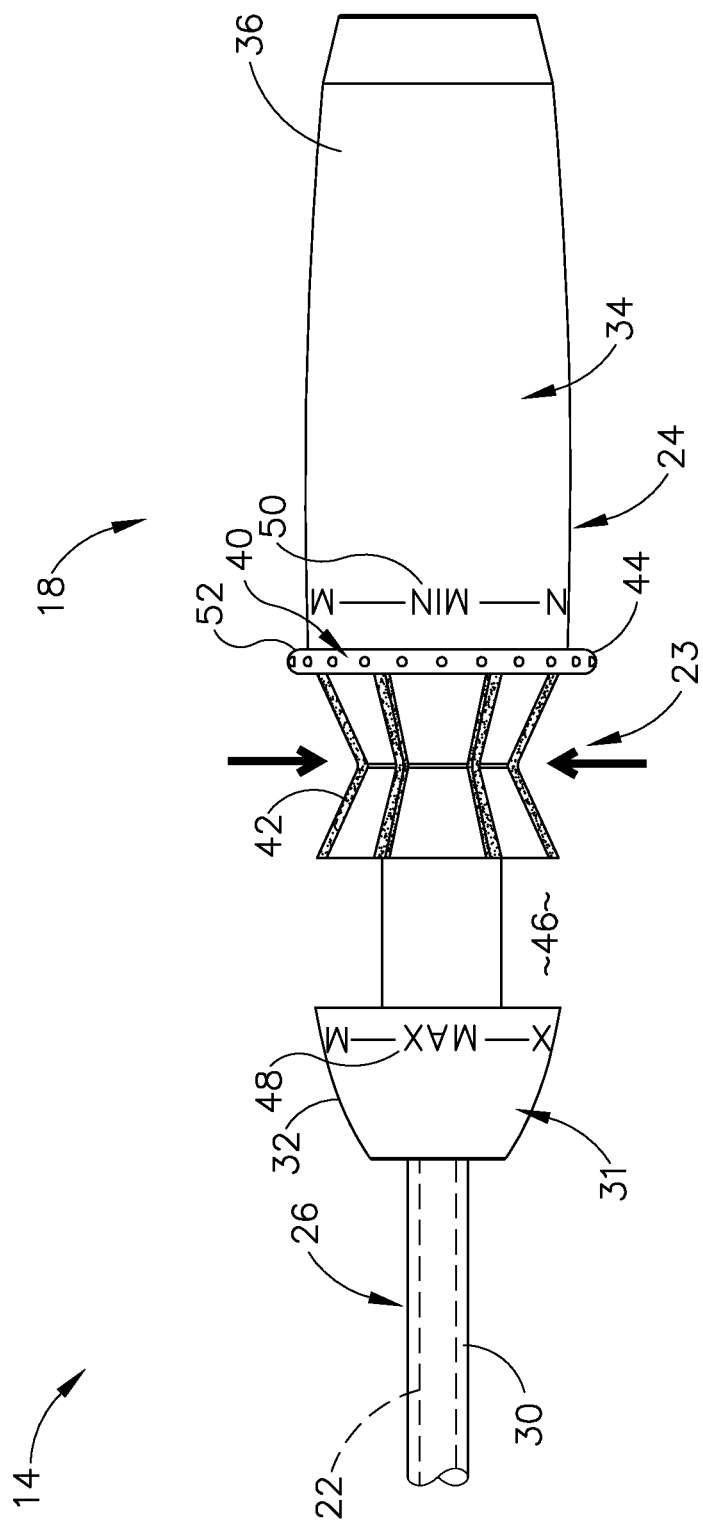
FIG. 4B depicts a top view of an activated handle assembly of the surgical instrument of FIG. 1, with the actuation assembly in the minimum power position and in an actuated state.

FIGS. 4A-4B show another example of the surgical instrument (14) in use to provide the low ultrasonic power level during the surgical procedure. With respect to FIG. 4A, the operator selects the low power position. If the actuation assembly (23) is not already in the low power position, the operator translates the actuation assembly (23) proximally to the proximal end of the annular groove (46) to select the low power position. To activate the blade (20) (see FIG. 1), the operator compresses the activation collar (42) from the expanded state, shown in FIG. 4A, to the contracted state in FIG. 4B in order to close the activation circuit in the control circuitry (not shown), as discussed above. The operator may then release the activation collar (42) to deactivate the blade (20). Alternatively, rather than release the activation collar (42) the operator may translate the actuation assembly (23) distally to the high power position to activate the blade (20) at the high ultrasonic power level. Of course, it will be appreciated that the activator ring (40) and the activation collar (42) may be engaged a variety of combinations for uniquely treating the patient during the surgical procedure. Thus, the specific operation of the surgical instrument (14) described herein is not intended to unnecessarily limit the invention.

D. Exemplary Alternative Actuation Assemblies

In some instances, it may be desirable to provide a surgical instrument (114) with an alternative form of actuation assembly (123). In particular, it may be desirable to provide the surgical instrument (114) with the actuation assembly (123) that includes an activator ring (140) that rotates about the longitudinal axis of an elongate body (134). In addition, it may also be desirable to provide the surgical instrument (114) with the actuation assembly (123) that includes the activation element in the form of an activation button (142) for activating the surgical instrument (114). Various examples of alternative actuation assemblies are described in greater detail below; while further examples will be apparent to those of ordinary skill in the art in view of the teachings herein. It should be understood that the various actuation assemblies described below may be readily incorporated into the surgical instrument (14) in place of the actuation assembly (23). As such, like numbers described below indicate like features described above.

Figure 5:
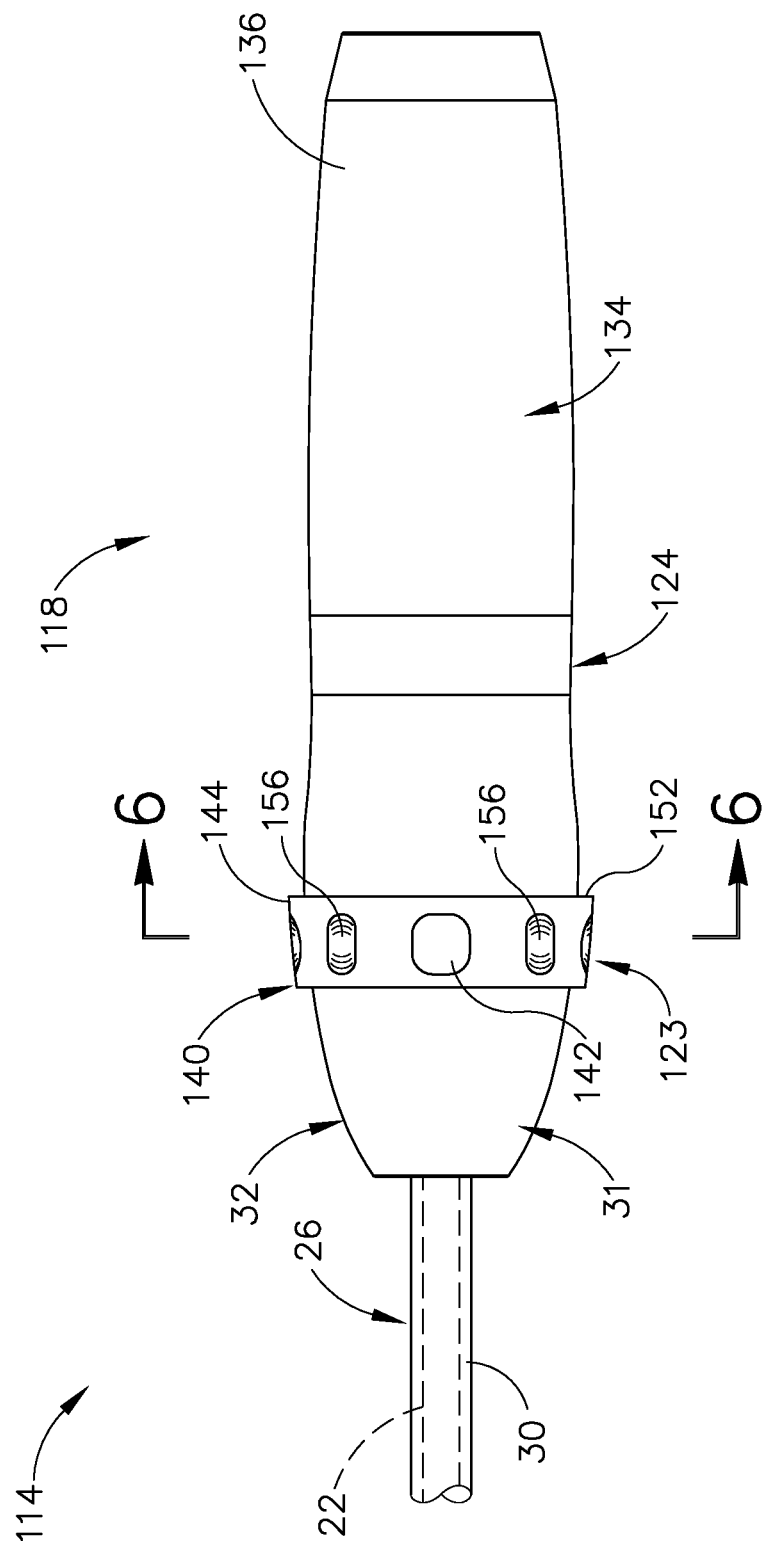
FIG. 5 depicts a top view of a handle assembly of another exemplary surgical instrument.
Figure 6:
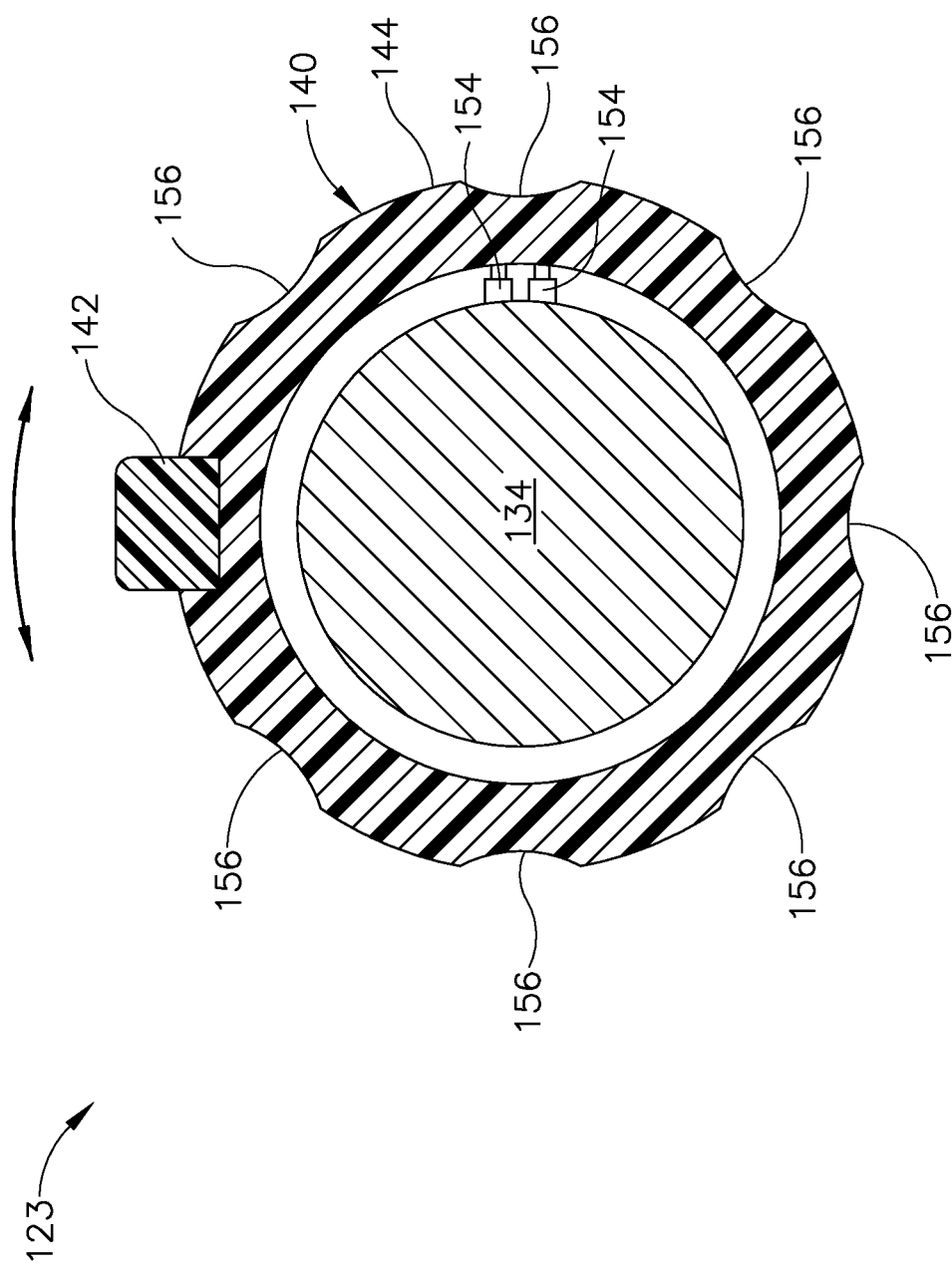
FIG. 6 depicts a cross-sectional view of the surgical instrument of FIG. 5 taken along section line 6-6 of FIG. 5.

FIGS. 5-6 show one merely illustrative example of a handpiece (118) and handle assembly (124) having the actuation assembly (123) for both selecting between at least two predetermined oscillations and activating the surgical instrument (114). The actuation assembly (123) includes an activator element in the form of an activator ring (140); and the activation element in the form of an activation button (142). The activation button (142) is operable to activate the ultrasonic transducer (21) (see FIG. 1) to thereby activate the blade (20) (see FIG. 1). To this end, the activator ring (140) freely rotates about the elongate body (134), while the activation button (142) actuates the activation switch (not shown) for directing the ultrasonic transducer to selectively drive the ultrasonic blade (20) (see FIG. 1) to vibrate ultrasonically during use.

The activator ring (44) generally surrounds the elongate body (134) and may be received within an annular groove (not shown) encircling the elongate body (134). The activator ring (144) similarly encircles the longitudinal axis and is coaxial with the longitudinal axis. In order to select between the at least two predetermined ultrasonic power levels while simultaneously activating the surgical instrument (114), the activation button (142) projects from the activator ring (44) and is selectively movable between a plurality of positions. By way of example, the activation button is selectively movable between a high position, a low position, and an off position. The activation button (142) in the high position actuates the activation switch (not shown) and directs the ultrasonic transducer (21) (see FIG. 1) to drive the blade (20) (see FIG. 1) at the high ultrasonic power level. The activation button (142) in the low position actuates the activation switch (not shown) further and directs the ultrasonic transducer (21) (see FIG. 1) to drive the blade (20) (see FIG. 1) at the low ultrasonic power level. In contrast, the activation button (142) in the off position inhibits activation of the ultrasonic transducer (21) (see FIG. 1) and thereby prevents ultrasonic oscillation of the blade (20) (see FIG. 1) during use. The high, low, and off positions described herein indicate unique modes of operating the surgical instrument (114) during the surgical procedure, such as with a high power predetermined oscillation and a low power predetermined oscillation. However, it will be appreciated that the high, low, and off positions may vary depending on the type of button and/or switch used in alternative examples. As such, the invention is not intended to be unnecessarily limited to the order and description of the high, low, and off positions provided herein.

In some versions, the activation button (142) includes a rocker switch (not shown) having electrically conductive features (not shown) for opening and closing the activation circuit in control circuitry (not shown) within the handpiece (118). The rocker switch (not shown) may rock distally and proximally for respectively closing the activation circuit in control circuitry (not shown) in order to activate the ultrasonic generator (21) (see FIG. 1) with the maximum and minimum predetermined power levels. Furthermore, the rocker switch (not shown) may remain in an intermediate position configured to open the activation circuit in control circuitry (not shown) and prevent activation of the ultrasonic generator (21). Alternatively, the activation button (142)

may include a slider switch (not shown) having other electrically conductive features (not shown) for opening and closing the activation circuit in control circuitry (not shown) within the handpiece (118). Like the rocker switch (not shown), the slider switch (not shown) may slide distally and proximally for respectively closing the activation circuit in control circuitry (not shown) in order to activate the ultrasonic generator (21) (see FIG. 1) with the maximum and minimum predetermined power levels. The slider switch (not shown) may also remain in an intermediate position configured to open the activation circuit in control circuitry (not shown) and prevent activation of the ultrasonic generator (21).

As described briefly above, the activator ring (44) is configured to freely rotate about the elongate body (134) such that the operator may position the activation button (142) in any desirable angular position about the elongate body (134). With respect to FIG. 6, the activation button (42) is operatively connected to the elongate body (134) and the activation switch (not shown) by a plurality of contact elements (154). Each of the contact elements (154) is configured to communicate the selection of the high ultrasonic power level or the low ultrasonic power level while still allowing the activator ring (140) to freely rotate about the elongate body (134). For example, the contact elements (154) shown in FIG. 6 are in the form of pogo pins for maintaining constant contact and electrical continuity with complementary contact features of the elongate body (134) during rotation of the activator ring (140).

With respect to FIGS. 5-6, the operator grips the actuation assembly (123) with at least one hand for rotating the actuation assembly (123) within the annular grove (not shown) to any desirable position for accessing the activation button (142). The operator has access to the actuation assembly (123) from around generally the entirety of the surgical instrument (114) given that the actuation assembly (23) generally surrounds the elongate body (134). In addition, the activator ring (140) further includes an annular lip (152) and a plurality of recesses (156) radially disposed about an outer circumferential surface (144) for providing additional grip.

In use, the operator selects from one of the high power, the low power, or the off positions to selectively operate the blade (20) (see FIG. 1) as described herein. The operator may also freely rotate the activator ring (140) while simultaneously activating or deactivating the surgical instrument (114) for treating the patient. Of course, it will be appreciated that the activator ring (140) and the activation button (142) may be respectively rotated and engaged in a variety of combinations for uniquely treating the patient during the surgical procedure. Thus, the specific operation of the surgical instrument (114) described herein is not intended to unnecessarily limit the invention.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic instrument for use during a surgical procedure, comprising: (a) a body defining a longitudinal axis and configured to receive an ultrasonic transducer for selectively generating an ultrasonic oscillation at a first predetermined power level and an ultrasonic oscillation at a second predetermined power level; (b) a shaft assembly projecting from the body, the shaft assembly including an acoustic waveguide configured to communicate the ultrasonic oscillation at the selected first or second predetermined power level therealong; (c) an ultrasonic blade connected to the acoustic waveguide such that the acoustic waveguide communicates the ultrasonic oscillation at the selected first or second predetermined power level to the ultrasonic blade; and (d) an actuation assembly connected to the body and configured to operatively connect to the ultrasonic transducer for selective operation of the ultrasonic blade, the actuation assembly comprising: (i) an activator ring having an outer circumferential surface generally surrounding the body and being selectively moveable relative to the body such that the activator ring is accessible to be gripped by an operator around an entirety of the outer circumferential surface, and (ii) an activation mechanism connected to the activator ring such that the activation mechanism is configured to selectively move relative to the body in conjunction with the activator ring, wherein at least a portion of the activation mechanism is configured to selectively activate the ultrasonic transducer to drive the ultrasonic blade at the selected first or second predetermined power level.

Example 2

The ultrasonic instrument of Example 1, wherein the activation mechanism further includes an activation collar extending longitudinally from the activator ring about the longitudinal axis, and the activation collar is configured to selectively activate the ultrasonic transducer to drive the ultrasonic blade at the selected first or second predetermined power level.

Example 3

The ultrasonic instrument of Example 2, wherein the activation collar is compressible from an expanded state to a contracted state such that in the expanded state the activation collar is configured to prevent the ultrasonic transducer from driving the ultrasonic blade, and in the contracted state the activation collar is configured to activate the ultrasonic transducer to drive the ultrasonic blade at the selected first or second predetermined power level.

Example 4

The ultrasonic instrument of any one or more of Examples 2 through 3, wherein the activation collar is radially biased outwardly from the longitudinal axis toward the expanded state.

Example 5

The ultrasonic instrument of any one or more of Examples 2 through 4, wherein the activator ring and the activation collar are translatably mounted to the body to selectively translate along the longitudinal axis between a first position and a second position such that compressing the activation collar to the contracted state in the first position is configured to direct the ultrasonic transducer to oscillate the ultrasonic blade with the ultrasonic oscillation at the first predetermined power level and compressing the activation collar to the contracted state in the second position is configured to direct the ultrasonic transducer to oscillate the ultrasonic blade with the ultrasonic oscillation at the second predetermined power level.

Example 6

The ultrasonic instrument of any one or more of Examples 1 through 5, wherein the first predetermined power level is a high predetermined power level and the second predetermined power level is a low predetermined power level.

Example 7

The ultrasonic instrument of any one or more of Examples 2 through 7, wherein the body further includes a first indicia and a second indicia, the first indicia is configured to indicate to the operator that the activator ring and the activation collar are in the first position for directing the ultrasonic blade to oscillate with the ultrasonic oscillation at the first predetermined power level, and the second indicia is configured to indicate to the operator that the activator ring and the activation collar are in the second position for directing the ultrasonic blade to oscillate with the ultrasonic oscillation at the second predetermined power level.

Example 8

The ultrasonic instrument of Example 7, wherein the first predetermined power level is a high predetermined power level, the second predetermined power level is a low predetermined power level, and the first indicia and the second indicia are configured to respectively indicate selection of the high and low predetermined power levels.

Example 9

The ultrasonic instrument of Example 1, wherein the activator ring is rotatably mounted to the body to rotate about the longitudinal axis, the activation mechanism further includes an activation button projecting from the activator ring, and the activation button is configured to selectively direct the ultrasonic transducer to oscillate with the ultrasonic oscillation at the selected first or second predetermined power level.

Example 10

The ultrasonic instrument of Example 9 wherein the first predetermined power level is a high predetermined power level and the second predetermined power level is a low predetermined power level.

Example 11

The ultrasonic instrument of any one or more of Examples 9 through 10, wherein the activator ring is configured to rotate freely around the body.

Example 12

The ultrasonic instrument of any one or more of Examples 1 through 11, wherein the activator ring further includes a plurality of contact elements projecting therefrom to the body, the plurality of contact elements configured to maintain electrical continuity between the rotatable activator ring and the body for electrical communication therebetween.

Example 13

The ultrasonic instrument of Example 12, wherein the plurality of contact elements includes a plurality of pogo pins.

Example 14

The ultrasonic instrument of any one or more of Examples 9 through 13, wherein the activation button is selectively movable between a first position, a second position, and a third position such that in the first position the activation button is configured to direct the ultrasonic transducer to oscillate the ultrasonic blade with the ultrasonic oscillation at the first predetermined power level, in the second position the activation button is configured to direct the ultrasonic transducer to oscillate the ultrasonic blade with the ultrasonic oscillation at the second predetermined power level, and in the third position the activation button is configured to prevent activation of the ultrasonic transducer.

Example 15

The ultrasonic instrument of any one or more of Examples 1 through 14, wherein the activator ring further includes a plurality of recesses angularly spaced about the outer circumferential surface for further being gripped by the operator.

Example 16

An ultrasonic instrument for use during a surgical procedure, comprising: (a) a body defining a longitudinal axis and configured to receive an ultrasonic transducer for selectively generating an ultrasonic oscillation at a first predetermined power level and an ultrasonic oscillation at a second predetermined power level; (b) a shaft assembly projecting from the body, the shaft assembly including an acoustic waveguide configured to communicate the ultrasonic oscillation at the selected first or second predetermined power level therealong; (c) an ultrasonic blade connected to the acoustic waveguide such that the acoustic waveguide communicates the ultrasonic oscillation at the selected first or second predetermined power level to the ultrasonic blade; and (d) an actuation assembly connected to the body and configured to operatively connect to the ultrasonic transducer for selective operation of the ultrasonic blade, the actuation assembly comprising: (i) an activator element being selectively moveable along the body such that the activator element is accessible to be gripped by an operator around an entirety of the outer circumferential surface; and (ii) an activation mechanism operatively connected to the activator element such that the activation mechanism is configured to selectively move along the body in conjunction with the activator element, wherein at least a portion of the activation mechanism is configured to selectively direct the ultrasonic transducer to oscillate the ultrasonic blade with the ultrasonic oscillation at the selected first or second predetermined power level.

Example 17

A method of operating an ultrasonic instrument during a surgical procedure, the ultrasonic instrument having a body, a shaft assembly, an ultrasonic blade, and an actuation assembly, the body defining a longitudinal axis and configured to receive an ultrasonic transducer for selectively generating an ultrasonic oscillation at a first predetermined power level and an ultrasonic oscillation at a second predetermined power level, the shaft assembly projecting from the body, the shaft assembly including an acoustic waveguide configured to communicate the selected first or second predetermined oscillation therealong, the ultrasonic blade connected to the acoustic waveguide such that the acoustic waveguide communicates the selected first or second predetermined oscillation to the ultrasonic blade, the actuation assembly connected to the body and configured to operatively connect to the ultrasonic transducer for selective operation of the ultrasonic blade, the actuation assembly having an activator element being selectively movable along the body such that the activator element is accessible to be gripped by an operator around an entirety of the outer circumferential surface, and an activation mechanism operatively connected to the activator element such that the activation mechanism selectively moves along the body in conjunction with the activator element, the method comprising: (a) gripping the activator element with at least one hand of the operator; (b) moving the activator element simultaneously with the activation mechanism relative to the body of the ultrasonic instrument; and (c) engaging the activation mechanism and directing the ultrasonic blade to oscillate with one of the first or second predetermined oscillations.

Example 18

The method of Example 17, wherein the activator element is an activator ring that generally surrounds the body, and the method further comprises: (a) moving the activator ring and the activation mechanism relative to the body between a first position and a second position; and (b) selecting at least one of the first position and the second position in order to respectively select the first predetermined oscillation or the second predetermined oscillation.

Example 19

The method of Example 18, wherein the activation mechanism further includes an activation collar extending longitudinally from the activator ring about the longitudinal axis, and engaging the activation mechanism further comprises: compressing the activation collar from an expanded state to a contracted state.

Example 20

The method of Example 17, wherein the activator element is an activator ring that generally surrounds the body, and the method further comprises: rotating the activator ring about the longitudinal axis and orienting the ultrasonic blade to a selected position during the surgical procedure.

IV. MISCELLANEOUS

While several of the examples described above include contact switches (not shown), it should be understood that any other suitable kind of switches may be used. Moreover, various other kinds of structures may be used to provide an electrical signal to the generator (12), to close a circuit between the generator (12) and the ultrasonic transducer (21), and/or to otherwise selectively activate the ultrasonic transducer (21) and/or the waveguide (22). Various suitable alternatives will be apparent to those of ordinary skill in the art in view of the teachings herein. It is contemplated that all of these alternatives are included within the meaning of the broad term "switch."

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic instrument for use during a surgical procedure, comprising:
   (a) a body defining a longitudinal axis, wherein the body is configured to support an ultrasonic transducer operable to generate ultrasonic energy at a first power level and at a second power level;
   (b) a shaft assembly extending distally from the body, wherein the shaft assembly includes an acoustic waveguide acoustically coupled with the ultrasonic transducer and configured to communicate the ultrasonic energy distally therealong;
   (c) an ultrasonic blade coupled to the acoustic waveguide and configured to communicate the ultrasonic energy to tissue positioned in contact with the ultrasonic blade; and
   (d) an activation member that at least partially encircles the body about the longitudinal axis, wherein the activation member is selectively actuatable between a first state in which the activation member is configured to inhibit activation of the ultrasonic transducer and a second state in which the activation member is configured to activate the ultrasonic transducer to energize the acoustic waveguide with ultrasonic energy,
   wherein the activation member is translatable relative to the body along the longitudinal axis between a first longitudinal position and a second longitudinal position, wherein the activation member in the first longitudinal position and the second state is configured to activate the ultrasonic transducer to generate ultrasonic energy at the first power level, wherein the activation member in the second longitudinal position and the second state is configured to activate the ultrasonic transducer to generate ultrasonic energy at the second power level, wherein the activation member is configured to define a first outer diameter in the first state and a second outer diameter in the second state, wherein the first outer diameter is different than the second outer diameter.

2. The ultrasonic instrument of claim 1, wherein the first power level is different than the second power level.

3. The ultrasonic instrument of claim 1, wherein the first state comprises a radially expanded state, wherein the second state comprises a radially contracted state.

4. The ultrasonic instrument of claim 3, wherein the activation member is biased toward the radially expanded state, wherein the activation member is compressible toward the radially contracted state.

5. The ultrasonic instrument of claim 1, wherein the activation member includes a collar.

6. The ultrasonic instrument of claim 1, wherein the body includes an annular groove, wherein the activation member is translatably disposed within the annular groove.

7. The ultrasonic instrument of claim 1, wherein the first longitudinal position comprises a proximal position and the second longitudinal position comprises a distal position.

8. The ultrasonic instrument of claim 1, wherein the activation member is further translatable to a third longitudinal position, wherein the ultrasonic transducer is configured to assume a deactivated state in response to the activation member assuming the third longitudinal position.

9. The ultrasonic instrument of claim 8, wherein the third longitudinal position is located between the first longitudinal position and the second longitudinal position.

10. The ultrasonic instrument of claim 1, further comprising a ring member secured to the activation member, wherein the ring member is translatable with the activation member between the first longitudinal position and the second longitudinal position.

11. The ultrasonic instrument of claim 10, wherein the ring member is configured to operatively couple with a first switch, wherein the activation member is configured to operatively couple with a second switch.

12. The ultrasonic instrument of claim 11, wherein the first switch includes a power level selector switch, wherein the second switch includes a power activation switch.

13. The ultrasonic instrument of claim 1, wherein the shaft assembly is selectively attachable to the body such that a proximal end of the acoustic waveguide couples with a distal end of the ultrasonic transducer.

14. The ultrasonic instrument of claim 13, further comprising a torqueing mechanism disposed distal to the activation member, wherein the torqueing mechanism is configured to limit an amount of torque applied between the acoustic waveguide and the ultrasonic transducer during attachment of the shaft assembly to the body.

15. An ultrasonic instrument for use during a surgical procedure, comprising:

(a) a body defining a longitudinal axis, wherein the body is configured to support an ultrasonic transducer operable to generate ultrasonic energy at a first power level and at a second power level;
(b) a shaft assembly extending distally from the body, wherein the shaft assembly includes an acoustic waveguide acoustically coupled with the ultrasonic transducer and configured to communicate the ultrasonic energy distally therealong;
(c) an ultrasonic blade coupled to the acoustic waveguide and configured to communicate the ultrasonic energy to tissue positioned in contact with the ultrasonic blade; and
(d) an activation member coupled to the body, wherein the activation member includes a pair of sides that are diametrically opposed about the longitudinal axis and are selectively actuatable relative to one another to transition the activation member between a first state in which the activation member is configured to inhibit activation of the ultrasonic transducer and a second state in which the activation member is configured to activate the ultrasonic transducer to energize the acoustic waveguide with ultrasonic energy,
wherein the activation member is longitudinally movable relative to the body between a first position and a second position, wherein the activation member in the first position and the second state is configured to activate the ultrasonic transducer to generate ultrasonic energy at the first power level, wherein the activation member in the second position and the second state is configured to activate the ultrasonic transducer to generate ultrasonic energy at the second power level.

16. The ultrasonic instrument of claim 15, wherein the activation member encircles the body about the longitudinal axis.

17. The ultrasonic instrument of claim 15, wherein the first state comprises a radially expanded state and the second state comprises a radially contracted state.

18. An ultrasonic instrument for use during a surgical procedure, comprising:
(a) a body defining a longitudinal axis, wherein the body is configured to support an ultrasonic transducer operable to generate ultrasonic energy at a first power level and at a second power level;
(b) a shaft assembly extending distally from the body, wherein the shaft assembly includes an acoustic waveguide acoustically coupled with the ultrasonic transducer and configured to communicate the ultrasonic energy distally therealong;
(c) an ultrasonic blade coupled to the acoustic waveguide and configured to communicate the ultrasonic energy to tissue positioned in contact with the ultrasonic blade;
(d) a ring member that encircles the body, wherein the ring member is movable relative to the body between a first position and a second position such that the ring member is translatable along the longitudinal axis; and
(e) an activation member secured to the ring member and movable with the ring member between the first and second positions, wherein the activation member is selectively actuatable relative to the ring member to activate the ultrasonic transducer to energize the acoustic waveguide with ultrasonic energy,
wherein the activation member is configured to activate the ultrasonic transducer to generate ultrasonic energy at the first power level in response to actuation of the activation member relative to the ring member in the first position,
wherein the activation member is configured to activate the ultrasonic transducer to generate ultrasonic energy at the second power level in response to actuation of the activation member relative to the ring member in the second position,
wherein the activation member is further translatable to a third position located between the first and second positions, wherein the activation member is configured to prevent activation of the ultrasonic transducer and the blade when the activation member is in the third position.

19. The ultrasonic instrument of claim 18, wherein the first power level is greater than the second power level.

20. The ultrasonic instrument of claim 19, wherein the first position is distal of the second position.

\* \* \* \* \*